United States Patent [19]
Chang et al.

[11] Patent Number: 5,447,522
[45] Date of Patent: Sep. 5, 1995

[54] CAPACITOR CHARGING CIRCUIT FOR IMPLANTABLE DEFIBRILLATOR

[75] Inventors: Yain N. Chang, Missouri City; Scott C. Mazoch, Guy, both of Tex.

[73] Assignee: Intermedics, Inc., Angleton, Tex.

[21] Appl. No.: 139,412

[22] Filed: Oct. 20, 1993

[51] Int. Cl.⁶ .............................................. A61N 1/39
[52] U.S. Cl. .............................................. 607/7; 607/4
[58] Field of Search .............................. 607/4, 5, 7

[56] References Cited

U.S. PATENT DOCUMENTS

| | | | |
|---|---|---|---|
| 3,442,269 | 5/1969 | Druz | 607/7 |
| 3,671,842 | 6/1972 | McKeown | 320/1 |
| 3,863,126 | 1/1975 | Colyn | 320/1 |
| 3,886,950 | 6/1975 | Ukkestad et al. | 128/419 D |
| 4,233,659 | 11/1980 | Pirkle | 363/134 |
| 4,548,209 | 10/1985 | Wielders et al. | 607/4 |
| 4,800,883 | 1/1989 | Winstrom | 607/7 |
| 5,285,779 | 2/1994 | Cameron et al. | 607/5 |

FOREIGN PATENT DOCUMENTS 2113031  7/1983  United Kingdom .

OTHER PUBLICATIONS

Motorola Data Sheet pp. 495–507 MC34129.

*Primary Examiner*—William E. Kamm
*Attorney, Agent, or Firm*—Richard L. Robinson

[57] ABSTRACT

An implantable defibrillator having a charging circuit for charging a high-voltage energy storage capacitor from a low voltage battery. Current from the battery is switched on and off through the primary winding of a voltage step-up transformer to induce a fly-back current in the secondary winding. The fly-back current is rectified and applied across the energy storage capacitor. The frequency of switching of the primary current is varied in relationship to the voltage of the battery to maintain a substantially constant average charging current as battery voltage decreases. Current through the primary is monitored on a cycle-by-cycle basis and switched off if it exceeds a preset limit.

15 Claims, 3 Drawing Sheets

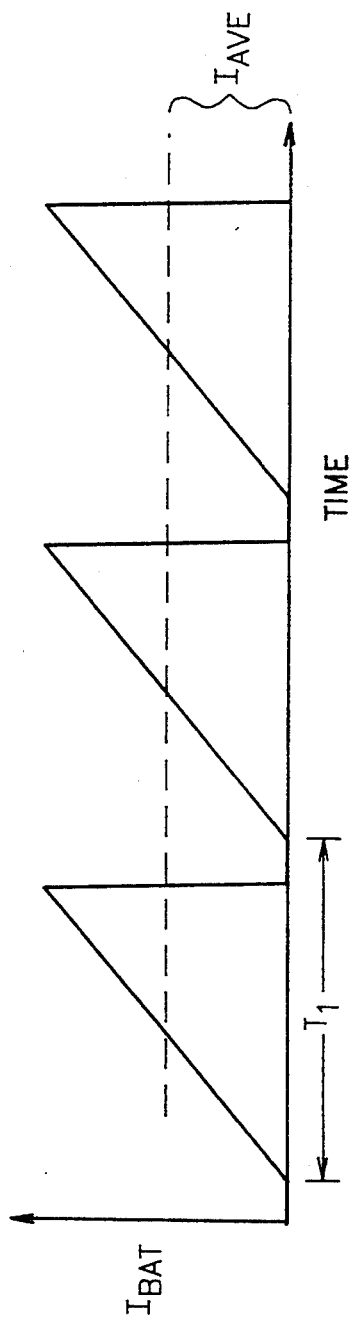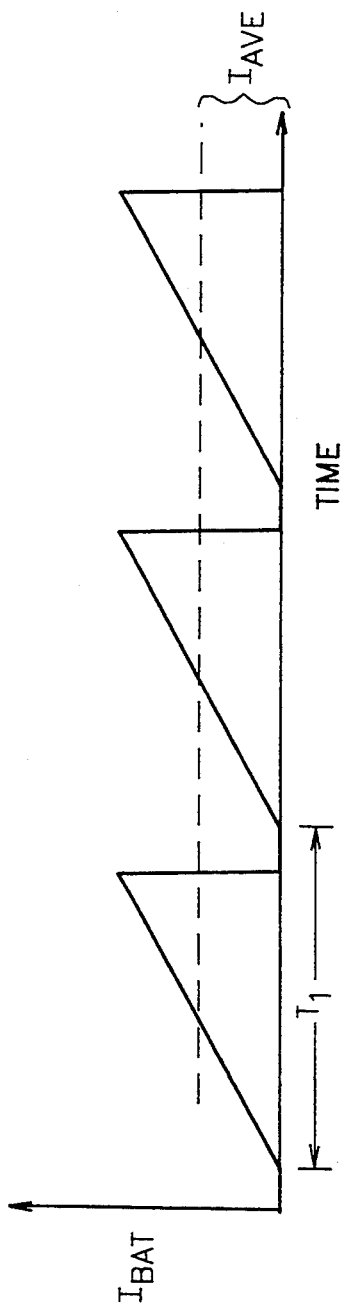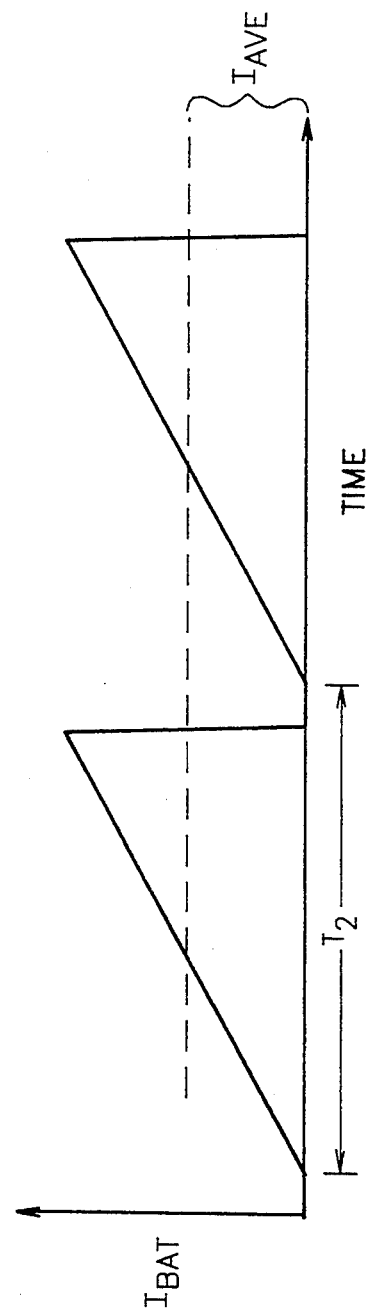

CAPACITOR CHARGING CIRCUIT FOR IMPLANTABLE DEFIBRILLATOR

BACKGROUND OF THE INVENTION

1. Field of the Invention

The present invention relates generally to implantable cardiac stimulators, and more particularly to a capacitor charging circuit in an implantable defibrillator.

2. Background Information

Implantable defibrillators are implanted in patients who can be identified as being likely to suffer cardiac arrhythmias, such as ventricular fibrillation, that can cause sudden death. The defibrillator detects the occurrence of ventricular fibrillation and automatically delivers defibrillating therapy. Implantable defibrillators in their most general form include appropriate electrical leads for collecting electrical signals generated by the heart, and for delivering electric shocks to the heart to provide defibrillation therapy. Also included are batteries, energy storage capacitors, and control circuitry connected to the leads, batteries and capacitors for sensing the electrical activity of the heart and for charging the capacitors and triggering the delivery of shocks through the leads. Implantable defibrillators can also include circuitry for providing cardioverting therapy for treating tachycardia, and for providing pacing therapy for treating bradycardia.

Defibrillation therapy generally involves rapid delivery of a relatively large amount of electrical energy to the heart at high voltage. Presently available batteries suitable for use in implantable defibrillators are not capable of delivering energy at such levels directly. Consequently, it is customary to provide a high-voltage energy storage capacitor that is charged from the battery via appropriate charging circuitry. To avoid wasting battery energy, the high-voltage energy storage capacitor is not maintained in a state of charge, but rather is charged during an interval after fibrillation has been identified by the control circuitry, and immediately prior to delivering the shock.

The charging circuitry in an implantable defibrillator sometimes involves switching circuitry for cyclicly interrupting DC current flow from the battery through the primary winding of a voltage step-up transformer in order to induce a transient current in the secondary winding of the transformer during the fly-back period. The induced fly-back current in the secondary winding is rectified and applied to the terminals of a high-voltage energy storage capacitor, thereby causing the energy storage capacitor to become fully charged over a number of switching cycles.

It is desirable that energy be transferred from the battery to the storage capacitor as efficiently as possible in order to reduce the time required to charge the high voltage storage capacitor. This avoids excessive delay in delivering therapy after fibrillation has been detected by the implantable defibrillator. Capacitor charging speed is affected by the fact that the voltage delivered by the battery to the charging circuitry drops over the life of the battery. In a conventional, fixed switching frequency charging circuit, as the battery voltage drops, the average current drawn from the battery during charging also drops over the life of the battery, resulting in an increase in the time required to charge the energy storage capacitor.

It is also desirable that current flow from the battery to the capacitor be limited during the initial charging period to avoid saturation of the step-up transformer and excessive current flow through the switching device. At the time that charging begins, the storage capacitor is initially in a state of discharge. Due to the volt-second product imbalance between the primary and secondary windings of the transformer, high current will be drawn from the battery until voltage starts to build up in the energy-storage capacitor.

SUMMARY OF THE INVENTION

In accordance with one aspect of the invention, an implantable defibrillator includes a battery, a voltage step-up transformer having a primary winding connected to the battery, and having a secondary winding, and a high-voltage energy storage capacitor connected to the secondary winding. A capacitor charger includes switching means in circuit communication with the battery and the primary winding for cyclicly permitting and interrupting current flow through the primary winding. Control means in circuit communication with the battery and with the switching means cause the switching means to cyclicly permit and interrupt current in such a manner that the average current remains substantially constant as the voltage of the battery decreases.

In accordance with another aspect of the invention, the capacitor charger includes current sensing means in circuit communication with the primary winding for sensing current flow through the primary winding. The control means is in circuit communication with the current sensing means and with the switching means and causes the switching means to interrupt current in response to sensed current flow exceeding a preset current limit. In accordance with yet another aspect of the present invention, a method of charging a high-voltage energy storage capacitor in an implantable defibrillator from a low voltage battery is presented. Current from the battery through the primary winding of a voltage step-up transformer is switched on and off to induce a fly-back transient current in a secondary winding of the transformer. This fly-back transient current is rectified and applied across the terminals of the high-voltage energy storage capacitor. The battery voltage is monitored and the rate of switching of current through the primary winding is varied in response to a decrease in battery voltage such that average current through the primary winding remains substantially constant as battery voltage decreases.

In accordance with still another aspect of the present invention, the method of charging the storage capacitor includes monitoring the current through the primary winding and switching off current through the primary winding in response to monitored current exceeding a predetermined limit.

It is an object of the present invention to provide an improved charging circuit for charging the high-voltage energy storage capacitor of an implantable defibrillator.

It is a further object of the present invention to avoid an increase in the time required to charge the high-voltage energy storage capacitor of an implantable defibrillator as battery voltage decreases as the battery becomes partially depleted.

It is another object of the present invention to avoid excessive current flow at the initiation of charging of the high-voltage energy storage capacitor of an implantable defibrillator where the capacitor is initially in a state of discharge.

Further objects and advantages of the present invention will be apparent from the following descriptions of a preferred embodiment with reference to the drawings.

BRIEF DESCRIPTION OF THE DRAWINGS

FIG. 3 is a graph of the current drawn from a new battery during charging of the energy storage capacitor in accordance with the prior art charging method.

FIG. 4 is a graph of the current drawn from a partially depleted battery during charging of the energy storage capacitor in accordance with the prior art charging method.

FIG. 5 is a graph of the current drawn from a partially depleted battery during charging of the energy storage capacitor in accordance with the present invention.

DESCRIPTION OF THE PREFERRED EMBODIMENT

Figure 1:
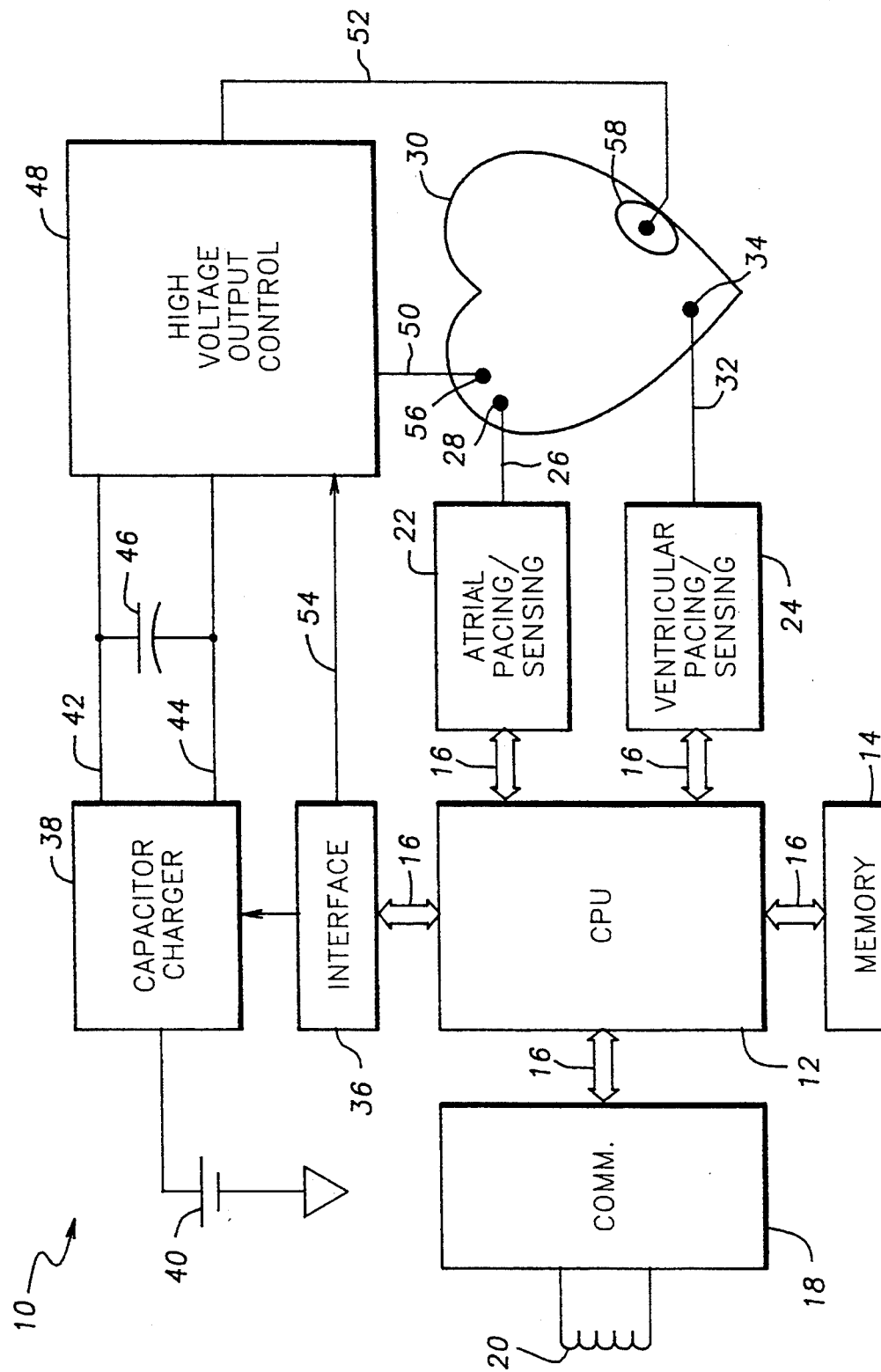
FIG. 1 is a block diagram of an implantable defibrillator in accordance with the present invention.

Referring to FIG. 1, there is illustrated a general block diagram of an implantable defibrillator 10 in accordance with the present invention. Defibrillator 10 is controlled by a digital central processing unit 12 operating under the control of software stored in memory unit 14. Central processing unit 12 and memory unit 14 communicate in well known fashion over data and address bus 16. Central processing unit 12 is programmed via an external programmer (not shown) that communicates with defibrillator 10 via communications unit 18. An antenna coil 20 connected to communications unit 18 receives electromagnetic energy radiated by a transmitter portion of the external programmer, with the electromagnetic energy being modulated so as to convey programming instructions. The received energy is demodulated in communications unit 18 and the data and programming instructions are passed on to CPU unit 12 over data and address bus 16. Antenna coil 20 also serves to radiate modulated electromagnetic energy from a transmitter portion of communications unit 18 to transfer data to the external programmer. Such data can convey information about the parameters and modes of defibrillator 10, and about sensed physiological information. Atrial pacing/sensing unit 22 and ventricular pacing/sensing unit 24 communicate with CPU unit 12 over data and address bus 16 to provide dual chamber pacing therapies in addition to the cardioversion and defibrillation therapies which are the principal objectives of defibrillator 10. An atrial lead 26 having one or more electrodes 28 for placement in an atrial chamber of heart 30 is electrically connected to atrial pacing/sensing unit 22 for delivering pacing pulses to the atrium, and for sensing naturally occurring depolarization signals and other signals for use by CPU unit 12 to regulate therapy. A ventricular lead 32 having one or more electrodes 34 for placement in a ventricular chamber of heart 30 is electrically connected to ventricular pacing/sensing unit 24 for delivering pacing pulses to the ventricle, and for sensing naturally occurring depolarization signals and other signals for use by CPU unit 12 to regulate therapy. It should be understood that leads 26 and 32 as shown are merely representative of a typical dual chamber pacing arrangement, and may be arranged for bipolar or unipolar pacing, or other pacing modes as are known in the art.

Defibrillation therapy is initiated by control signals from CPU unit 12 applied over data and address bus 16 to high voltage interface 36. Interface 36, among other things, isolates the high voltage portions of defibrillator 10 from CPU unit 12 and the other low voltage circuitry. Control signals buffered by interface 36 are applied to capacitor charger unit 38 having an input line connected to battery 40 and a pair of high voltage output lines 42 and 44 connected to high-voltage energy storage capacitor 46. It should be appreciated that while battery 40 is shown connected only to capacitor charger 38 in the simplified block diagram of FIG. 1, battery 40 also supplies power for all of the active devices of the digital and analog circuitry of defibrillator 10. Lines 42 and 44 also connect energy storage capacitor 46 to high voltage output control unit 48, which controls the delivery of the high voltage charge from capacitor 46 to defibrillation leads 50 and 52 in response to control signals received from interface 36 on line 54. Leads 50 and 52 are provided with one or more endocardial electrodes 56 and one or more patch electrodes 58. It should be understood that leads 50 and 52 as shown are merely representative of a typical defibrillation lead arrangement, and may be arranged differently according to other defibrillating modes as are known in the art.

Figure 2:
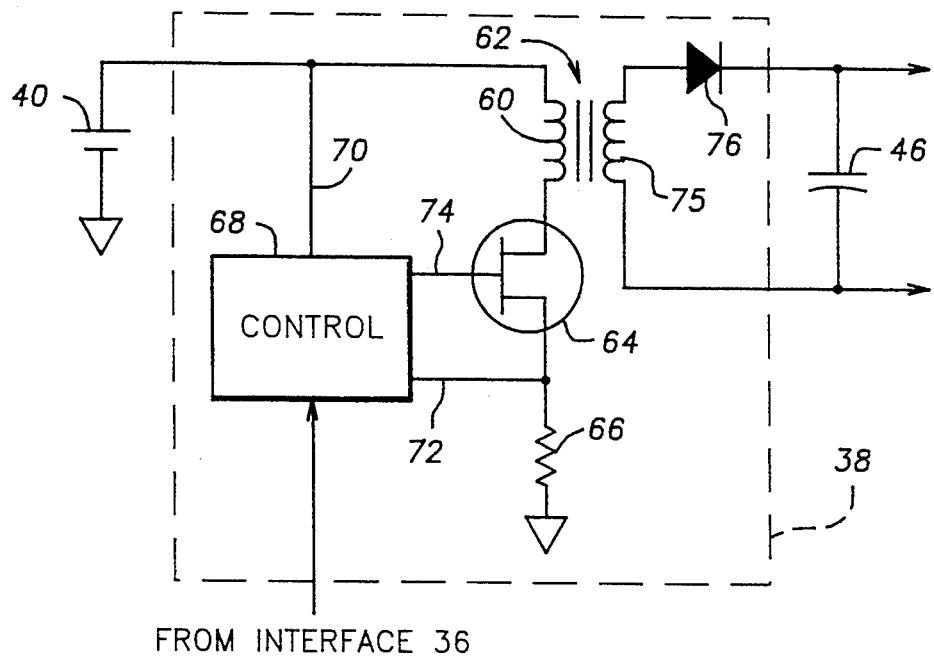
FIG. 2 is a simplified schematic diagram of the capacitor charger block of FIG. 1.

Referring to FIG. 2, there is shown a simplified schematic diagram of capacitor charger 38 illustrating the general principles of the invention. The positive terminal of battery 40 is connected to one terminal of the primary winding 60 of step-up transformer 62. The negative terminal of battery 40 is connected to ground. The other terminal of primary winding 60 is connected to the drain terminal of FET transistor 64. The source terminal of FET transistor 64 is connected through current-sense resistor 66 to ground. Thus, it can be appreciated that the flow of current from battery 40 through primary winding 60 can be controlled by FET transistor 64. Control circuit 68 has a first input line 70 connected to battery 40 for the purpose of monitoring the output voltage of battery 40, and a second input line 72 for the purpose of monitoring the voltage drop across current-sense resistor 66 and thus the current through primary winding 60. Control circuit 68 has an output line 74 connected to the gate terminal of FET transistor 64. Upon receipt of a control signal from interface 36, control circuit 68 applies a periodically varying voltage to the gate of FET transistor 64 through line 74 to cause FET transistor 64 to be repeatedly switched on and off at a selected frequency, thereby causing current through primary winding 60 to vary in accordance with the switching frequency. For each switching cycle, energy is stored into the primary winding 60 of transformer 62 during the time that FET transistor 64 is on. Immediately after FET transistor 64 turns off, a transient fly-back current will be induced in secondary winding 75 of step-up transformer 62. The transient current in the secondary winding 75 is rectified by diode 76 and the rectified current is applied across the terminals of high-voltage energy storage capacitor 46.

Control circuit 68 functions to vary the switching frequency of FET transistor 64 as a function of the voltage of battery 40 as sensed through input line 70. As the battery voltage drops, the switching frequency is decreased in order to maintain the average current drawn from battery 40 at a relatively constant level, as explained further below. Control circuit 68 also functions to limit the maximum current that is permitted to flow through primary winding 60 on a cycle-by-cycle basis to prevent transformer 62 from saturating. Saturation is particularly likely during the initial charging cycles when capacitor 46 is in a state of discharge.

Referring to FIG. 3, there is illustrated in graphical form the current drawn from the battery of an implantable defibrillator in accordance with the prior art where the battery is new and providing its maximum output voltage. Current drawn from the battery is graphed on the vertical axis as $I_{BAT}$ and appears as a sawtooth waveform with a cycle-to-cycle period of $T_1$. The switching frequency of the capacitor charger is selected such that at a cycle length of $T_1$, the average current $I_{AVE}$ that is drawn from the battery does not exceed the current rating of the battery, thereby ensuring maximum lifespan of the battery.

Referring now to FIG. 4, there is illustrated the situation that occurs in the prior art where the battery is no longer new and its output voltage has dropped, and the switching frequency remains fixed. The cycle length remains at $T_1$, but the current slope is decreased in accordance with the equation $$V = L \frac{\delta I}{\delta T}.$$

As a result of the lower voltage, $I_{AVE}$ in FIG. 4 is lower than in FIG. 3, which means that less power is being transferred from the battery to the storage capacitor of the implantable defibrillator. That results in an increase in the time necessary to fully charge the storage capacitor, which delays delivery of defibrillating therapy. This undesirable situation is overcome by the present invention.

Referring now to FIG. 5, there is illustrated the situation that results from application of the principles of the present invention to the prior art problem illustrated in FIGS. 3 and 4. FIG. 5 assumes that the battery is no longer new and has a reduced output voltage that is the same as the situation illustrated in FIG. 4. However, the switching frequency has been decreased as a function of the battery voltage such that the cycle length $T_2$ is now long enough to permit the current to reach the same peak value, and thus average value, as in the new battery situation illustrated in FIG. 3. With the present invention, the rate at which energy is delivered by the battery during charging of the storage capacitor remains relatively constant over the life of the battery, thereby avoiding an increase in charging time as the battery becomes partially depleted.

Figure 6:
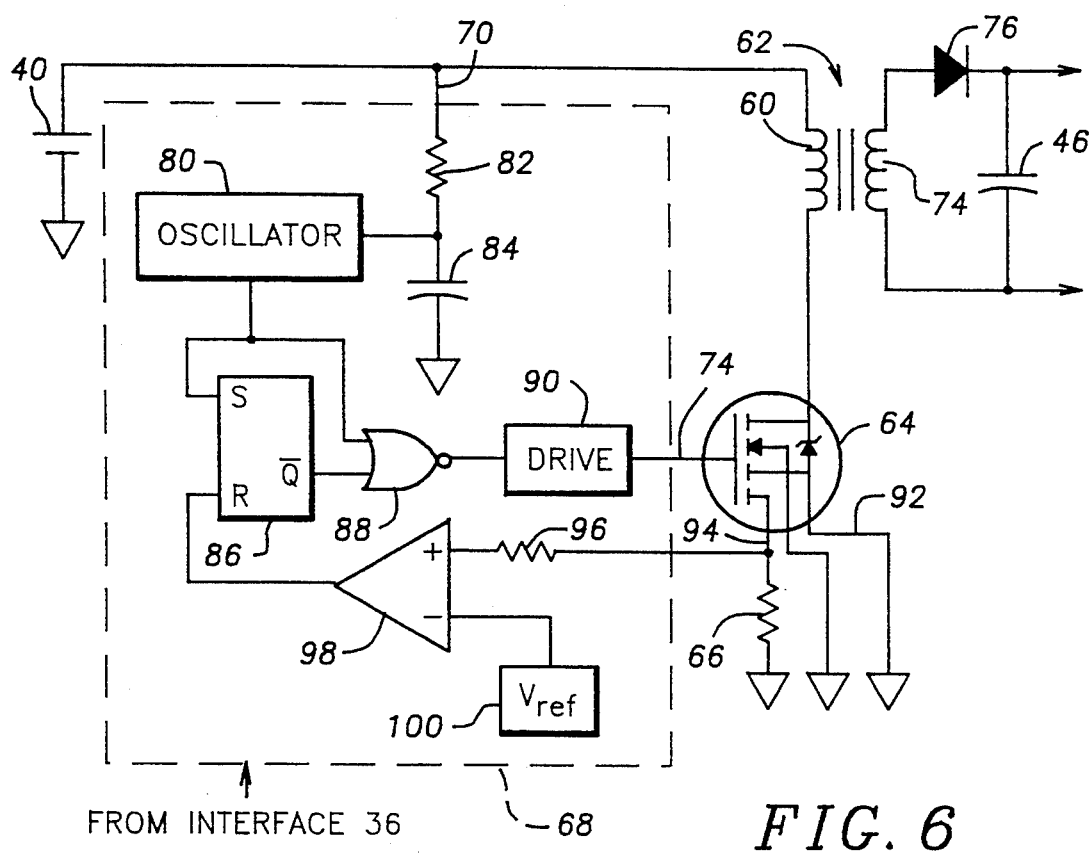
FIG. 6 is a more detailed schematic diagram of the capacitor charger block of FIG. 1.

Referring to FIG. 6, there is illustrated in more detail the capacitor charger of FIG. 2. FIG. 6 differs from FIG. 2 primarily in that FET transistor 64 is shown in its preferred form as a SENSEFET which is a specialized but well known form of FET transistor having a sense terminal through which a small amount of current flows in a fixed ratio relative to the current flow through the source terminal. SENSEFET's are commercially available from International Rectifier, Motorola, and others. In addition, FIG. 6 shows control circuit 68 of FIG. 2 in greater detail.

Control circuit 68 includes an oscillator 80 having a frequency of oscillation determined by the RC time constant set by timing resistor 82 and timing capacitor 84. The frequency of oscillation is also determined by the voltage of battery 40 as applied to resistor 82 through line 70. The output of oscillator 80 is connected to the "set" input terminal S of flip-flop 86 and to one input terminal of NOR gate 88. The $\overline{Q}$ output terminal of flip-flop 86 is connected to the other input terminal of NOR gate 88. The output terminal of NOR gate 88 is connected to drive buffer 90, which in turn has an output terminal connected via line 74 to the gate terminal of SENSEFET 64. The source terminal 92 of SENSEFET 64 is connected to ground, whereas the sense terminal 94 of SENSEFET 64 is connected to one terminal of current sense resistor 66. The other terminal of resistor 66 is connected to ground. The junction of sense resistor 66 and sense terminal 94 is connected through current limiting resistor 96 to the non-inverting input of comparator 98. A fixed voltage reference $V_{REF}$ 100 has its output connected to the inverting input of comparator 98. The output of comparator 98 is connected to the "reset" terminal of flip-flop 86.

Control circuit 68 causes energy storage capacitor 46 to start charging upon receipt of a command signal from interface 36 under control of CPU 12. In the preferred embodiment, the charge command signal consists of applying power to the circuitry of control circuit 68. Oscillator 80 begins oscillating at the frequency determined by the voltage of battery 40 and the fixed values of resistor 82 and capacitor 84, and generates a train of pulses of short duration relative to the cycle period. With a new battery 40, the frequency of oscillation is about 200 kHz. With each high output pulse of oscillator 80, a high state is presented directly to one input of NOR gate 88, resulting in a low state at the output of NOR gate 88 for the duration of that oscillator pulse. The drive signal to the gate of SENSEFET 64 correspondingly goes low, and SENSEFET 64 is switched off for the duration of the oscillator pulse. The high output pulse from oscillator 80 is also applied to "set" input S of flip-flop 86, resulting in the $\overline{Q}$ output of flip-flop 86 being latched in a low state. As the trailing edge of the oscillator pulse goes low, both inputs to NOR gate 88 become low, the output of NOR gate 88 goes high, and SENSEFET 64 is switched on. SENSEFET 64 remains in a conducting state until the rising edge of the next output pulse from oscillator 80 is generated, at which point SENSEFET 64 is switched off for the duration of the oscillator pulse, and the cycle repeats. It can thus be seen that SENSEFET 64 is cyclicly switched off for a short period relative to the on-time of each cycle at a frequency determined by oscillator 80. The current drawn from battery 40 follows the pattern illustrated in FIG. 3 when the battery 40 is new.

As the battery 40 becomes depleted over its lifespan, its output voltage drops, resulting in a decrease in the frequency of oscillation of oscillator 80. It can be understood intuitively that as the voltage of battery 40 as applied to resistor 82 via line 70 drops, timing capacitor 84 will tend to charge more slowly, resulting in a decrease in the frequency of oscillation. The current drawn from battery 40 will thus follow the pattern illustrated in FIG. 5 as battery 40 ages. In other words, as the battery voltage drops, the charging frequency drops proportionally. Over the useful life of the battery, the output voltage can drop by approximately 50%, resulting in an approximate halving of the charging frequency from about 200 kHz to about 100 kHz.

Under certain conditions it is desirable to limit the maximum current drawn from battery 40. In particular, during the beginning of the charging period, the current drawn absent current limiting could exceed the saturation point of transformer 62, and could conceivably exceed the current rating of SENSEFET 64. Therefore, current through SENSEFET 64 is monitored by comparator 98 by comparing the voltage across resistor 66 to fixed voltage reference 100. Because of the internal design of SENSEFET 64, the current through resistor 66 is a small fraction of the current through source terminal 92, with a ratio of approximately 1:3000. Voltage reference 100 provides a voltage value selected to represent the maximum desirable current through source terminal 92. When the voltage monitored across resistor 66 exceeds the reference voltage, the output of comparator 98 goes high, presenting a high state to the "reset" input of flip-flop 86. That causes the $\overline{Q}$ output of flip-flop 86 to be latched in a high state such that the following input to NOR gate 88 is high. The output of NOR gate 88 therefore goes low, switching off SENSEFET 64 until it is switched on again by the trailing edge of the next oscillator pulse. It should be understood that current is monitored and limited, if necessary, on a cycle-by-cycle basis. In other words, so long as the current never exceeds the preset limit in any particular charging cycle, SENSEFET 64 is switched off briefly only upon generation of the next output pulse from oscillator 80. If, however, the current as sensed at resistor 66 should exceed the preset limit during any particular cycle, SENSEFET 64 is switched off by comparator 98 as soon as the current exceeds the limit, and SENSEFET 64 then remains off for the remainder of the present cycle. It is therefore assured that excessive current draw will cause an override of the switching control which is otherwise a function of battery voltage only.

The several component elements of control circuit 68, such as oscillator 80, flip-flop 86, NOR gate 88, drive buffer 90, comparator 98 and voltage reference 100 can be implemented using well known, readily available discrete components. However, these functions are conveniently available in a single commercially available integrated circuit manufactured by Motorola and sold under part number MC33129 as a high performance current mode controller.

While the present invention has been illustrated and described with particularity in terms of a preferred embodiment, it should be understood that no limitation of the scope of the invention is intended thereby. The scope of the invention is defined only by the claims appended hereto. It should also be understood that variations of the particular embodiments described herein incorporating the principles of the present invention will occur to those of ordinary skill in the art and yet be within the scope of the appended claims.

What is claimed is:

1. In an implantable defibrillator sized for implantation within a living human patient, having a battery, a voltage step-up transformer having a primary winding connected to said battery, and having a secondary winding, a high-voltage energy storage capacitor connected to said secondary winding, and a lead and an electrode each sized for implantation within a living human patient in proximity to cardiac tissue, said electrode being electrically connected to said high-voltage storage capacitor via said lead, the improvement comprising a capacitor charger including:

switching means in circuit communication with said battery and said primary winding for interrupting current flow through said primary winding; and control means in circuit communication with said battery and with said switching means, and directly responsive to the voltage of said battery, for causing said switching means to interrupt current cyclicly at a frequency that is variable as a function of the voltage of said battery throughout the useful life of said battery.

2. The implantable defibrillator of claim 1, in which said control means includes means for generating a sequence of alternating on signals and off signals, said switching means being responsive to said on and off signals.

3. The implantable defibrillator of claim 2, in which said means for generating a sequence of alternating on signals and off signals generates at least said off signals at a frequency that is related to the voltage of said battery.

4. The implantable defibrillator of claim 3, in which said means for generating a sequence of alternating on signals and off signals generates at least said off signals at a frequency that decreases as the voltage of said battery decreases.

5. In an implantable defibrillator sized for implantation within a living human patient, having a battery, a voltage step-up transformer having a primary winding connected to said battery, and having a secondary winding, a high-voltage energy storage capacitor connected to said secondary winding, and a lead and an electrode each sized for implantation within a living human patient in proximity to cardiac tissue, said electrode being electrically connected to said high-voltage storage capacitor via said lead, the improvement comprising a capacitor charger including:

switching means in circuit communication with said battery and said primary winding for cyclicly permitting and interrupting current flow through said primary winding; and control means in circuit communication with said battery and with said switching means, and directly responsive to the voltage of said battery, for causing said switching means to cyclicly permit and interrupt current such that the on-time of each cycle is variable as a function of the voltage of said battery throughout the useful life of said battery.

6. The implantable defibrillator of claim 5, in which said control means includes means for generating a sequence of alternating on signals and off signals, said switching means being responsive to said on and off signals.

7. The implantable defibrillator of claim 6, in which said means for generating a sequence of alternating on signals and off signals varies the period between an on signal and a subsequent off signal in response to the voltage of said battery.

8. The implantable defibrillator of claim 7, in which said means for generating a sequence of alternating on signals and off signals increases the period between an on signal and a subsequent off signal as the voltage of said battery decreases.

9. In an implantable defibrillator sized for implantation within a living human patient, having a battery, a voltage step-up transformer having a primary winding connected to said battery, and having a secondary winding, a high-voltage energy storage capacitor connected to said secondary winding, and a lead and an electrode each sized for implantation within a living human patient in proximity to cardiac tissue, said electrode being electrically connected to said high-voltage storage capacitor via said lead, the improvement comprising a capacitor charger including:

switching means in circuit communication with said battery and said primary winding for cyclicly permitting and interrupting current flow through said primary winding; and control means in circuit communication with said battery and with said switching means, and directly responsive to the voltage of said battery, for causing said switching means to cyclicly permit and interrupt current such that the average current is substantially constant as the voltage of said battery decreases throughout the useful life of said battery.

10. The implantable defibrillator of claim 9, in which said control means includes means for generating a sequence of alternating on signals and off signals, said switching means being responsive to said on and off signals.

11. The implantable defibrillator of claim 10, in which said means for generating a sequence of alternating on signals and off signals varies the period between an on signal and a subsequent off signal in response to the voltage of said battery.

12. The implantable defibrillator of claim 11, in which said means for generating a sequence of alternating on signals and off signals increases the period between an on signal and a subsequent off signal as the voltage of said battery decreases.

13. In an implantable defibrillator sized for implantation within a living human patient, having a battery, a voltage step-up transformer having primary and secondary windings, a high-voltage energy storage capacitor connected to said secondary winding, and a lead and an electrode each sized for implantation within a living human patient in proximity to cardiac tissue, said electrode being electrically connected to said high-voltage storage .capacitor via said lead, the improvement comprising a capacitor charger including:

switching means in circuit communication with said battery and said primary winding for interrupting current flow from said battery through said primary winding;

current sensing means in circuit communication with said primary winding for sensing current flow through said primary winding; and control means in circuit communication with said battery and with said switching means, and directly responsive to the voltage of said battery, for causing said switching means to interrupt current cyclicly at a frequency that is variable as a function of the voltage of said battery throughout the useful life of said battery, said control means further being in circuit communication with said current sensing means for causing said switching means to interrupt current in response to sensed current flow exceeding a preset current limit.

14. A method of charging a high-voltage energy storage capacitor in an implantable defibrillator from a low voltage battery, said high-voltage energy storage capacitor having electrical terminals and said implantable defibrillator including a voltage step-up transformer having a primary winding and a secondary winding, comprising the steps of:

switching on and off current from said battery through said primary winding of said voltage step-up transformer to induce a fly-back current in said secondary winding of said transformer;

rectifying said fly-back current and applying said rectified current across the terminals of said high-voltage energy storage capacitor; and monitoring the voltage of said battery and varying the rate of switching of current through said primary winding in response to a decrease in battery voltage such that average current through said primary winding remains substantially constant as battery voltage decreases.

15. The method of claim 14, and further including the step of:

monitoring the current through said primary winding and switching off current through said primary winding in response to monitored current exceeding a predetermined limit.

* * * * *